United States Patent [19]

Hernestam et al.

[11] 4,021,564

[45] May 3, 1977

[54] NEUROLEPTIC PIPERIDINE COMPOUNDS

[75] Inventors: Sven Erik Harry Hernestam, Malmo; Anders Karl Konrad Björk, Bjarred; Aina Lisbeth Abramo, Malmo; Bengt Erik Sigvard Kjellberg, Staffanstorp, all of Sweden

[73] Assignee: AB Ferrosan, Malmo, Sweden

[22] Filed: May 3, 1976

[21] Appl. No.: 682,582

[30] Foreign Application Priority Data

May 7, 1975 United Kingdom ............ 19222/75

[52] U.S. Cl. .......................... 424/267; 260/293.8; 260/293.67
[51] Int. Cl.² ................................. C07D 211/50
[58] Field of Search ................ 260/293.8; 424/267

[56] References Cited

UNITED STATES PATENTS

| 3,029,244 | 4/1962 | Lyle et al. | 260/293.8 |
| 3,438,991 | 4/1969 | Janssen et al. | 260/293.8 |
| 3,462,444 | 8/1969 | Beckett et al. | 260/293.8 |

FOREIGN PATENTS OR APPLICATIONS

| 47-18878 | 9/1972 | Japan | 260/293.8 |

Primary Examiner—Norma S. Milestone
Attorney, Agent, or Firm—Gordon W. Hueschen

[57] ABSTRACT

Novel 1-substituted-4-aroyl-4-hydroxy and -4-acyloxypiperidines and acid addition salts thereof, useful as central nervous system depressants and neuroleptics with pronounced antipsychotic effects, are disclosed. Methods of making same, pharmaceutical compositions thereof, a method of treating therewith, and important and novel intermediates for the production thereof, are also disclosed.

32 Claims, No Drawings

NEUROLEPTIC PIPERIDINE COMPOUNDS

BACKGROUND OF INVENTION

1. Field of Invention

1-Substituted-4-aroyl-4-hydroxy and -4-acyloxypiperidines and acid addition salts thereof; central nervous system depressant, neuroleptic compounds; compositions thereof; method of treating therewith; production thereof; intermediates therefor.

2. Prior Art

A number of ketones of the general formula

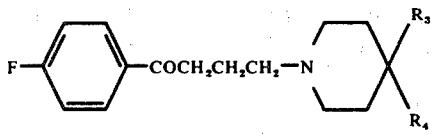

wherein $R_3$ and $R_4$ are widely different groups, have been made and tested. As to these type compounds, Janssen (Cavallito, "Structure-Activity Relationships I", page 37) has stated that one of the groups $R_3$ and $R_4$ must be aromatic and that only one may be hydrogen if the ketone is to be an anti-psychotic.

Three clinically-established compounds in this field are as follows, namely:

Haloperidol, of the foregoing formula, wherein $R_3 =$ OH and $R_4 =$

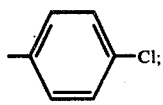

Chlorpromazine, having the formula

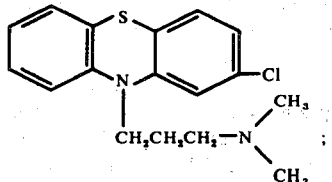

and Pimozide, having the formula

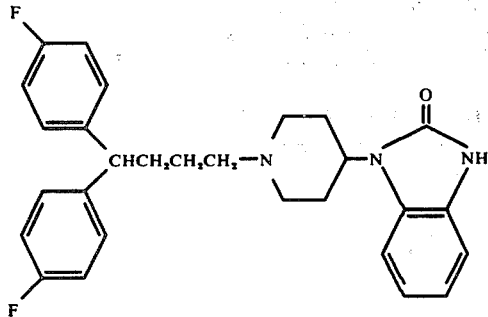

These established clinically-useful compounds of the prior art have, however, been found to be characterized by pronounced shortcomings and side-effects, and there is a clear demand for more specific and advantageous compounds in this activity and utility area, especially central nervous system depressants and neuroleptics with pronounced antipsychotic effect. The fulfillment of this demand is one of the objects of the present invention, as will become more fully apparent hereinafter.

SUMMARY OF THE INVENTION

This invention relates to novel 1-substituted-4-aroyl-4-hydroxy and 4-acyloxypiperidines, acid addition salts thereof, pharmaceutical compositions containing the same, a method of using the same as central nervous system depressants and neuroleptics, and a process for the manufacture thereof, as well as novel intermediates in the production thereof. The novel compounds provided by the present invention are selected from the group consisting of (a) 1-[3-(substituted benzoyl)-propyl]-4-(substituted benzoyl)-4-hydroxy or -4-acyloxypiperidines having the General Formula I:

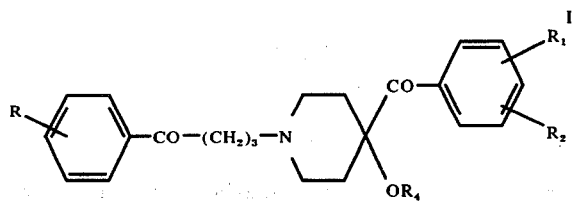

wherein $R_1$ and $R_2$ independently represent hydrogen or loweralkyl with 1 to 5 carbon atoms, inclusive, halogen including F, Cl, and Br, lower-alkoxy having 1 to 5 carbon atoms, inclusive, or $-CF_3$, and $R_4$ represents hydrogen or an acyl (Ac) group having 2 to 19 carbon atoms, inclusive, and R represents a halogen atom, e.g., F, Cl, or Br, or $-CF_3$, and b. acid addition salts thereof.

These novel compounds of Formula I have valuable pharmacological properties, especially as central nervous system depressants and neuroleptics having pronounced antipsychotic effects, all as more fully elucidated hereinafter.

OBJECTS

It is an object of the present invention to provide certain novel 1-substituted-4-aroyl-4-hydroxy and 4-acyloxypiperidines and acid addition salts thereof, which are useful as central depressants and neuroleptics, a process for producing the same, pharmaceutical compositions thereof, intermediates therefor, and a method of treating therewith. Additional objects will become apparent hereinafter, and still others will be obvious to one skilled in the art.

PREPARATION:

According to the present invention, the novel compounds of General Formula I are prepared according to any of the following reaction sequences:

Sequence A a.

by reacting a 4-benzoyl-4-hydroxypiperidine of Formula II:

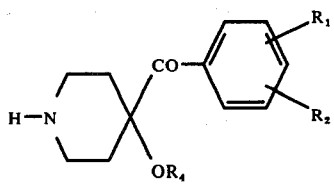

with a 1-substituted-3-(substituted benzoyl)propane compound of Formula III:

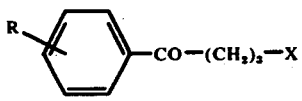

wherein X is a group or atom which is reactive with the hydrogen at the one position of the piperidine ring of II, e.g., halogen, preferably Br, or a reactive group, e.g., benzenesulfonyl or tosyl esters. to produce a compound of Formula I.

Sequence A *b*.

by reacting the 4-benzoyl-4-hydroxypiperidine (II) with an alkylene ketal of 1-substituted-3-(substituted benzoyl)-propane compound of Formula IV

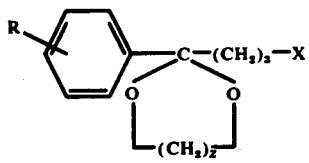

wherein Z is a small whole number, e.g., 2 or 3, and wherein X is the same as in III, e.g., halogen, preferably Br, or another reactive group, e.g., benzene sulfonyl or tosyl esters, to produce a 1-[3-(substituted benzoyl)-propyl]-4-(substituted benzoyl)-4-hydroxy-piperidine ketal compound of Formula V:

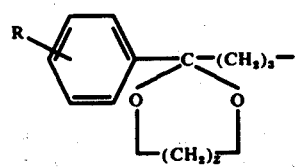

and hydrolyzing the compound of Formula V in conventional manner to produce a compound of Formula I.

The novel 4-benzoyl-4-hydroxypiperidines of Formula II which are employed in the method of the invention can be prepared by a sequence of reactions according to any of the following:

Sequence B *a*.

a Friedel-Crafts reaction of a compound of Formula VI, which is the acid chloride of 1-acetylisonipecotic acid or 1-methylisonipecotic acid, in turn readily derived from isonipecotic acid by conventional procedure:

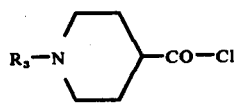

where $R_3$ is acetyl or methyl, and an $R_1R_2$-substituted benzene in a suitable reaction solvent, e.g., nitrobenzene or an excess of the reacting compound $R_1R_2$-benzene, to produce a compound of Formula VII:

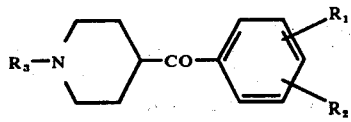

whereupon the acetyl group may be readily removed, if desired, with 5N HCl, to yield a compound of Formula VII ($R_3$ = H). Compound VII, then,(Sequence B, part B *a*)) is thus synthesized according to Duncan, R. C. et al., J. Med. Chem. 13, 1 (1970) ($R_3$ = $CH_3CO$), or according to Lyle, R. E. et al., J. Org. Chem 24, 330 (1959) ($R_3$ = $CH_3$).

Sequence B *b*.

a Grignard reaction of 4-cyanopyridine and a suitable known phenyl magnesium bromide or other halide to produce a compound of Formula VIII:

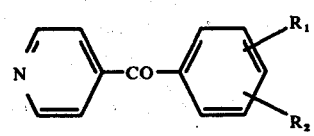

which 4-benzoylpyridine VIII is then either (a) hydrogenated over platinum catalyst to give the 4-piperidylarylcarbinol of Formula IX

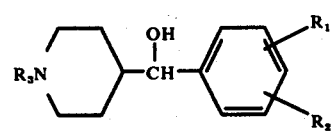

wherein $R_3$ represents hydrogen, or (b) first benzylated or methylated to the corresponding 1-benzyl- or 1-methyl- 4-aroylpyridinum halide and then reduced in the same manner to compound IX ($R_3$ = benzyl or $CH_3$). Compound IX is oxidized by chromic oxide or another oxidizing agent to produce a compound of Formula VII ($R_3$ = H, $CH_3$, or benzyl).

This synthesis of Compound VII [Sequence B *b*)] is according to U.S. Pat. No. 3,632,767 ($R_3$ = H). Only minor changes have been made in the method described therein. Representative Preparations (Preparations 8 – 10) are provided hereinafter for the production of Compound VII, e.g., wherein $R_1$ is hydrogen and $R_2$ is $CF_3$.

The preparation of Compound VII ($R_1$ = H, $R_2$ = $CF_3$, $R_3$ = acyl, e.g., $CH_3CO$) is particularly described in Preparation 11. See also Preparation 3.

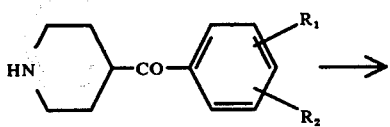

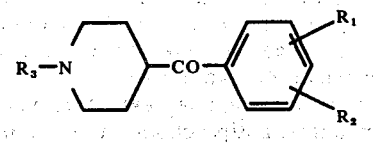

The crude 4-aroylpiperidine VII ($R_3 = CH_3$ or benzyl) is converted to the hydrobromide. Compound VII ($R_3 = H$) is acetylated. Compound VII ($R_3 = CH_3$, $CH_3CO$, benzyl) is dissolved in a suitable solvent, e.g., chloroform or carbon tetrachloride, and brominated with $Br_2$ to produce a compound of Formula X:

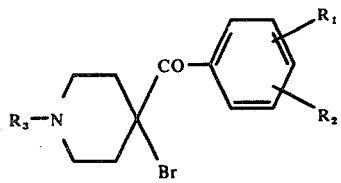

which, after recrystallization, is treated with sodium methoxide in methanol. After addition of water and evaporation of methanol, the compound of Formula XI:

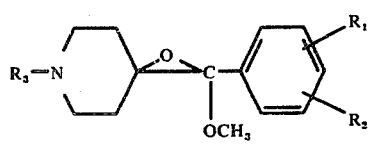

may be extracted with ether. The crude compound XI is hydrolized in ethanol with concentrated hydrochloric acid to produce a compound of Formula XII:

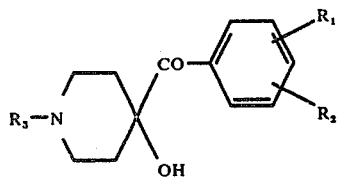

Compound XII ($R_3 = CH_3CO$) is precipitated with water. After alkalization, extraction with chloroform or benzene, and drying of the solution with sodium sulfate, compound XII ($R_3 = CH_3$ or benzyl) can be precipitated as an acid addition salt. The novel compounds of Formula II can be prepared from compound XII by:
C a. removal of the acetyl group (XII, $R_3 = CH_3CO$) using 5-N HCl. Other strong mineral acids may also be used,
C b. selective hydrogenolysis over palladium catalyst of the benzyl group (XII, $R_3$ = benzyl),
C c. demethylation (XII, $R_3 = CH_3$) with ethyl chloroformate followed by acid hydrolysis. In reactions A a) and A b), the compound of Formula II is reacted with a compound of Formula III or IV in a suitable solvent, either a nonpolar solvent, e.g., benzene or xylene, or a polar solvent, e.g., dimethylformamide or isobutyl acetate. The reaction is preferably performed in the presence of an acid binding agent, e.g., a tertiary amine such as triethylamine or potassium carbonate, and advantageously but not necessarily in an autoclave at 75° – 150° C.

After the coupling reaction, the compounds of Formula I are generally treated with water or 1-N NaOH and extracted with ether, methyl-butyl ketone, or the like. From the dried solution, salts with pharmaceutically acceptable acids, e.g., hydrochloric, hydrobromic, fumaric, citric, maleic, tartaric, or lactic or the like may be precipitated with acid in conventional manner and recrystallized. An acid salt, even if not pharmaceutically acceptable, is still useful, since it can readily be converted to another salt which is pharmaceutically acceptable in known manner, e.g., alkalization and then acidification with a different acid, if desired.

Of the described methods, A a) - [B a) or B b) ] - C a) is preferred, and the synthesis of the desired product can always be carried out by employment of such method. Procedure B b) is general, but B a) is preferred over B b).

The 4-acyloxy compounds of any Formula I type compound, preferably an alkanoyloxy, phenylalkanoyloxy, e.g., phenylpropionoxy, phenylacetoxy, or benzoyloxy derivative of such compound, as set forth in Table III, are formed by treating the 4-hydroxy compound of type I with a selected carboxylic acid anhydride, e.g., acetic, propionic, butyric, valeric, benzoic, phenylacetic, dimethylbenzoic, phenylpropionic, caproic, octanoic, decanoic, dodecanoic, hexadecanoic, or nonadecanoic acid anhydride, using a 4-dialkylaminopyridine as acylation catalyst. Triethyamine or other tertiary amine is used to bind the acid formed in the reaction. As a reaction medium there may be used, e.g., a non-protic solvent, excess triethylamine, or excess anhydride.

Some starting compounds and intermediates which may be used in preparing compounds according to the present invention are disclosed in an earlier copending U.S. application of some of us, viz., Serial No. 601,412, filed August 4, 1975, the disclosure of which is hereby incorporated by reference.

DETAILED DESCRIPTION OF THE INVENTION

The following Preparations and Examples are given by way of illustration only.

PREPARATION 1: 1-ACETYLISONIPECOTIC ACID AND ITS ACID CHLORIDE (VI)

A solution of 64.6 g (0.5 mole) of isonipecotic acid in 200 ml of acetic anhydride was refluxed for two hours and allowed to stir at room temperature overnight. The solution was concentrated and the residue which remained was triturated in ether. The solid was collected by filtration and recrystallized from isopropyl alcohol - isopropyl ether. Yield 58.2 g, melting point 178°–182° C. (Reference: Duncan, R. L., et al., J. Med. Chem. 13 (1), 1 [1970]). This compound is converted to its acid chloride by the following detailed procedure:

To 400 ml of $SOCl_2$ was added 68.9 g (0.4 mole) of 1-acetylisonipecotic acid, which dissolved.*)The acid chloride precipitated from solution and 1 liter of pentane was added. The mixture was filtered and the solid residue was washed several times with pentane. The solid was dried. Yield 72 g.

\*) The mixture was allowed to stir at room temperature for 1 hour.

PREPARATION 2: 1-ACETYL-4-(-p-FLUOROBENZOYL)PIPERIDINE (VII)

To a stirring mixture of 55.0 g (0.41 mole) of aluminum chloride in 100 ml. fluorobenzene was slowly added forty grams (0.21 mole) of 1-acetyl-isonipecotoyl chloride. After the addition was complete, the mixture was refluxed for one hour. The mixture was poured onto ice and the two resulting layers were separated. The aqueous layer was extracted with chloroform and the extracts were added to the fluorobenzene. The organic solution was dried over sodium sulfate and filtered. The filtrate was concentrated under reduced pressure and the residue was a crystalline solid. The reaction product was purified by recrystallization in ligroin-isopropylether. Yield 38.2 g, melting point 76°–80° C. (Reference: Duncan, R. L., et al., J. Med. Chem. 13 (1) 1 [1970]).

In the same manner, the following additional compounds were prepared, starting only from the appropriate benzene:

1-acetyl-4-benzoylpiperidine from benzene itself;
1-acetyl-4-(p-methoxybenzoyl)piperidine from methoxybenzene;
1-acetyl-4-(p-bromobenzoyl)piperidine from bromobenzene;
1-acetyl-4-(p-chlorobenzoyl)piperidine from chlorobenzene;
1-acetyl-4-(p-methylbenzoyl)piperidine from methylbenzene; and
1-acetyl-4-(3,4-dimethylbenzoyl)piperidine from 1,2-dimethylbenzene.

PREPARATION 3:
4-(p-FLUOROBENZOYL)PIPERIDINE HYDROCHLORIDE(VII)

A solution of 50 g (0.2 mole) of 1-acetyl-4-(p-fluorobenzoyl)piperidine in 200 ml of six Normal hydrochloric acid was refluxed for twelve hours. The cooled solution was extracted twice with benzene. The benzene extracts were dried ($Na_2SO_4$) and filtered. The filtrate was concentrated under reduced pressure, and the residual oil was converted to the hydrochloride salt. The crude product was recrystallized from isopropyl alcohol. Yield 42 g, melting point 223°–225° C. (Reference: Duncan, R. L. et al., J. Med. Chem. 13 (1) 1 [1970]).

In the same manner, the following additional compounds are prepared by substituting the appropriate starting 1-acetyl-4-benzoylpiperidine from Preparations 2 or 11 in the procedure of Preparation 3:

|  | m.p. |
|---|---|
| 4-benzoylpiperidine hydrochloride | 222–224° C. |
| 4-(p-methoxybenzoyl)piperidine hydrochloride | 255–258° C. |
| 4-(p-bromobenzoyl)piperidine hydrochloride | 228–230° C. |
| 4-(p-chlorobenzoyl)piperidine hydrochloride |  |
| 4-(p-methylbenzoyl)piperidine hydrochloride | 260–263° C. |
| 4-(3,4-dimethylbenzoyl)piperidine hydrochloride, |  | and many others.

PREPARATION 4:
1-ACETYL-4-BROMO-4-(p-FLUOROBENZOYL)-PIPERIDINE (X)

A solution of 36 g (0.145 mole) of 1-acetyl-4-(p-fluorobenzoyl)piperidine in 175 ml of chloroform was treated with fifteen ml of bromine. The mixture was heated at reflux for one hour and then allowed to stand overnight at room temperature. 1-Acetyl-4-bromo-4-(p-fluorobenzoyl)piperidine precipitated and was collected by filtration and recrystallized from ethanol. Yield 40.6 g, melting point 156°–159° C. In the same manner, additional intermediates of this type are produced by substituting the selected starting materials from Preparation 2 or 11 in the procedure of Preparation 4.

PREPARATION 5:
6-ACETYL-2-(p-FLUOROPHENYL)-2-METHOXY-1-OX-6-AZASPIRO [2.5] OCTANE (XI)

32.8 g (0.1 mole) of 1-acetyl-4-bromo-4-(p-fluorobenzoyl)piperidine was added to a solution of sodium methoxide prepared from 12.8 g of sodium in 400 ml of methanol. The mixture was heated at reflux for two hours. Water was added and the methanol was removed under reduced pressure. The aqueous layer was extracted with ether and the extracts were dried over sodium carbonate. Removal of the ether gave crude 6-acetyl-2-(p-fluorophenyl)-2-methoxy-1-ox-6-azaspiro [2.5] octane. Yield 24.2 g. In the same manner, additional intermediates of this type are produced by substituting the selected starting materials from Preparation 4 in the procedure of Preparation 5.

PREPARATION 6:
1-ACETYL-4-(p-FLUOROBENZOYL)-4-HYDROXYPIPERIDINE (XII)

A mixture of 21.3 g (0.076 mole) of 6-acetyl-2-(p-fluorophenyl)-2-methoxy-1-ox-6-azaspiro [2.5] -octane, 140 ml of ethanol and 27 ml of concentrated hydrochloric acid was stirred for fifteen minutes. Water was added. The solid which precipitated was collected by filtration and recrystallized from ethanol-ether giving nineteen grams of 1-acetyl-4-(p-fluorobenzoyl)-4-hydroxypiperidine. Melting point 146°–149° C. In the same manner, additional intermediates of this type are produced by substituting the selected starting materials from Preparation 5 in the procedure of Preparation 6.

PREPARATION 7:
4-(p-FLUOROBENZOYL)-4-HYDROXYPIPERIDINE HYDROCHLORIDE (II)

A solution of 18.6 g (0.07 mole) of 1-acetyl-4-(p-fluorobenzoyl)-4-hydroxypiperidine in 60 ml of 5-N HCl was refluxed for fifteen hours. Most of the water was removed under reduced pressure. Ethanol was added and the solution was cooled. The solid which precipitated was collected by filtration and recrystallized from ethanol giving 16.5 g of 4-(p-fluorobenzoyl)-4-hydroxypiperidine hydrochloride. Melting point 241°–243° C.

In the same manner, the following additional compounds are prepared by substituting the appropriate starting 1-acetyl-4-benzoyl-4-hydroxypiperidine from Preparation 6 in the procedure of Preparation 7:

4-benzoyl-4-hydroxypiperidine hydrochloride
4-(p-methoxybenzoyl)-4-hydroxypiperidine hydrochloride
4-(p-bromobenzoyl)-4-hydroxypiperidine hydrochloride
4-(m-trifluoromethylbenzoyl)-4-hydroxypiperidine hydrochloride
4-(3-trifluoromethyl-4-chlorobenzoyl)-4-hydroxypiperidine hydrochloride.
4-(p-chlorobenzoyl)-4-hydroxypiperidine hydrochloride
4-(p-methylbenzoyl)-4-hydroxypiperidine hydrochloride
4-(3,4-dimethylbenzoyl)-4-hydroxypiperidine hydrochloride
4-(3,4-dichlorobenzoyl)-4-hydroxypiperidine hydrochloride
and many others.

PREPARATION 8:
4-(m-TRIFLUOROMETHYLBENZOYL)PYRIDINE (VIII)

To a cold Grignard reagent prepared from 27 g (1.1 moles) of magnesium and 240 g (1.07 moles) of 3-bromobenzotrifluoride in 300 ml of dry ether and 150 ml of benzene, was added dropwise over a period of three hours a solution of 100 g (0.96 mole) of 4-cyanopyridine in 300 ml of benzene and 200 ml of ether. After being allowed to stand overnight at room temperature, the mixture was warmed for thirty minutes and then decomposed by adding 700 ml of saturated ammonium chloride solution. The ether-benzene layer was separated and extracted with 10% hydrochloric acid. The acid layer was separated and made basic with 20% sodium hydroxide and extracted with ether. The ether layer was dried over sodium sulphate. The ether solution was concentrated and the residual oil distilled to give 137 g (55%) of 4-(m-trifluoromethylbenzoyl)pyridine. Boiling point 97°–100° C/0.1 mm Hg. $n_D^{22} = 1.5380$.

PREPARATION 9:
4-(alpha-HYDROXY-m-TRIFLUOROMETHYLBENZYL)PIPERIDINE (IX)

A solution of 25.1 g (0.1 mole) of 4-(m-trifluoromethylbenzoyl)pyridine in 150 ml methanol and 10 ml concentrated hydrochloric acid was shaken with one gram of platinum oxide at an initial pressure of fifty psi of hydrogen. The hydrogen uptake was complete in ten hours. The catalyst was filtered off. After removal of the methanol under reduced pressure, the residue was dissolved in water and made basic with sodium hydroxide. Extraction with benzene and concentration of the benzene solution gave crude 4-(alpha-hydroxy-m-trifluoromethylbenzyl)piperidine. Yield 20.2 grams.

PREPARATION 10:
4-(m-TRIFLUOROMETHYLBENZOYL)PIPERIDINE (VII)

To a cold solution of 51.8 g (0.2 mole) of 4-(alphahydroxy-m-trifluoromethylbenzyl)piperidine in 200 ml of acetic acid was added dropwise a solution of sixteen g (0.16 mole) of chromic oxide in 100 ml acetic acid and twenty ml water. The mixture was allowed to stand at room temperature for sixteen hours. The solution was concentrated in vacuum and the residue taken up in water, made basic with sodium hydroxide, and extracted with benzene. The benzene solution was dried and concentrated. The crude oil was converted to the hydrochloride. Recrystallization from ethanol gave forty grams of 4-(m-trifluoromethylbenzoyl)piperidine hydrochloride. M.p. 197°–199° C.

Numerous other 4-(substituted benzoyl)piperidines are prepared from the appropriate correspondingly-substituted pyridine VIII) in the same manner.

PREPARATION 11:
1-ACETYL-4-(m-TRIFLUOROMETHYLBENZOYL)PIPERIDINE (VII)

To a solution of 32.1 g (0.125 mole) of 4-(m-trifluoromethylbenzoyl)piperidine in 75 ml of benzene and 21.2 g (0.2 mole) of $Na_2CO_3$, was added dropwise a solution of ten g (0.127 mole) of acetyl chloride in 75 ml of benzene. The mixture was refluxed for 2 hours. The mixture was filtered and the filtrate was concentrated under vacuum giving crude 1-acetyl-4-(m-trifluoromethylbenzoyl)piperidine. Yield 37.3 grams.

1-Acetyl derivatives of other compounds of Formula VII, $R_3 = H$, are prepared in this same manner, or in the manner of Preparation 2. These compounds are used as starting materials in the procedures of Preparations 3 or 4.

PREPARATION 12:
GAMMA-CHLORO-p-FLUOROBUTYROPHENONE AND ITS ETHYLENE GLYCOL KETAL (III and IV)

The synthesis of Compound III is according to C. van de Westeringh et al., Industrie chimique Belge 25, 1073 (1960).

The synthesis of Compound IV is according to Belgian Patent 668,124 (CA 65, 3800 h).

The titled compounds are well-known in the art.

PREPARATION 13:
4-ANISOYL-4-HYDROXYPIPERIDINE HYDROCHLORIDE (VII)[Cb]

Five-tenths grams of 10% Pd-C catalyst was added to 4.9 grams of 4-anisoyl-4-hydroxy-1-benzyl-piperidine hydrochloride in 50 ml. of ethanol. The mixture was shaken for twenty-four hours at a pressure of 20 psi of hydrogen. The mixture was filtered and concentrated. The reaction product was purified by recrystallization from ethanol. Yield: 3.5 grams, melting point 218°–220° C.

PREPARATION 14:
4-ACETOXY-4-(p-FLUOROBENZOYL)-1-METHYLPIPERIDINE HYDROCHLORIDE (VII) (Cc)

11.8 grams (0.05 mole) of 4-(p-fluorobenzoyl)-4-hydroxy-1-methyl piperidine was dissolved in 150 ml. of acetic anhydride at 90° C. The mixture was slowly heated to 150° C. and was kept at that temperature for one hour. The mixture was cooled and concentrated. The resulting oil was converted to the hydrochloride. The reaction product was purified by recrystallization from ethanol. Yield: 11.5 grams, melting point 274°–276° C.

PREPARATION 15:
4-(p-fluorobenzoyl)-4-HYDROXYPIPERIDINE HYDROCHLORIDE (VII) (Cc)

To 27.9 grams (0.1 mole) of 4-acetoxy-4-(p-fluorobenzoyl)-1-methylpiperidine in 200 ml. of benzene was added 27.1 (0.25 mole) of ethyl chloroformate. The mixture was refluxed for 48 hours. The mixture was extracted with $H_2O$, the organic solution was dried ($MgSO_4$) and filtered. The filtrate was concentrated. To the resulting oil was added 250 ml. of 6 Normal HCl and the mixture was refluxed for seventy-two hours. Most of the water was removed under reduced pressure. Ethanol was added and the solution cooled. The solid which precipitated was collected by filtration and recrystallized from ethanol giving eighteen grams of 4-(p-fluorobenzoyl)-4-hydroxypiperidine hydrochloride. Melting point 241°–243° C.

In the same manner, the procedure of Preparations 13, 14, and 15 is employed to produce other starting compounds within the scope of Formula VII wherein $R_3$ is hydrogen.

EXAMPLE 1:
1-[3-(p-FLUOROBENZOYL)PROPYL]-4-(p-FLUOROBENZOYL)-4-HYDROXYPIPERIDINE HYDROCHLORIDE (I)

A stirred mixture of eleven grams (0.05 mole) of 4-(p-fluorobenzoyl)-4-hydroxypiperidine, 14.7 grams (0.06 mole) of gamma-chloro-p-fluorobutyrophenone ethylene glycol ketal, 20 grams of anhydrous potassium carbonate, and 300 ml of isobutylacetate was heated at reflux for 48 hours. The mixture was filtered and the filtrate concentrated under vacuum. The residual oil was stirred with 75 ml of six Normal hydrochloric acid and 225 of ethanol for 1 hour. Water was added and most of the ethanol was removed under reduced pressure. The solid which precipitated was collected by filtration and recrystallized from ethanol to give 14.8 grams of 1-[3-(p-fluorobenzoyl)propyl]-4-(p-fluorobenzoyl)-4-hydroxypiperidine hydrochloride. Melting point 219°–221° C.

Propylene glycol and other lower-alkylene glycols can also be used in the method of the foregoing Example in place of ethylene glycol. Ethylene glycol is preferred.

This compound of Example 1 is converted to additional acid addition salts in conventional manner by neutralization and acidification with the selected acid according to the general procedure given hereinbefore.

In the same manner, the following additional compounds of Type I and their acid addition salts, e.g., their hydrochlorides, hydrobromides, citrates, or tartrates, are prepared by employing the selected starting compounds of Formulas II and III or II and IV from Preparations 7 and 12 in the procedure of Example 1:

- 1-[3-(p-fluorobenzoyl)propyl]-4-(p-methylbenzoyl)-4-hydroxypiperidine.
- 1-[3-(p-fluorobenzoyl)propyl]-4-(p-methoxybenzoyl)-4-hydroxypiperidine.
- 1-[3-p-fluorobenzoyl)propyl]-4-(p-bromobenzoyl)-4-hydroxypiperidine.
- 1-[3-(p-fluorobenzoyl)propyl]-4-(m-trifluoromethylbenzoyl)-4-hydroxypiperidine.
- 1-[3-(p-fluorobenzoyl)propyl]-4-(3-trifluoromethyl-4-chlorobenzoyl)-4-hydroxypiperidine.
- 1-[3-(p-fluorobenzoyl)propyl]-4-benzoyl-4-hydroxypiperidine.
- 1-[3-(p-fluorobenzoyl)propyl]-4-(p-chlorobenzoyl)-4-hydroxypiperidine.
- 1-[3-(p-fluorobenzoyl)propyl]-4-(3,4-dichlorobenzoyl)-4-hydroxypiperidine.
- 1-[3-(p-fluorobenzoyl)propyl]-4-(3,4-dimethylbenzoyl)-4-hydroxypiperidine, and the like.

EXAMPLE 2:
1-[3-(p-FLUOROBENZOYL)PROPYL]-4-(p-FLUOROBENZOYL)-4-HYDROXYPIPERIDINE HYDROCHLORIDE.

A stirred mixture of eleven grams (0.05 mole) of 4-(p-fluorobenzoyl)-4-hydroxypiperidine, fourteen grams (0.07 mole) of gamma-chloro-p-fluorobutyrophenone, seventeen grams of anhydrous sodium carbonate and 300 mls of isobutylacetate was heated at reflux for 48 hours. The mixture was filtered and the filtrate was concentrated under vacuum. The residual oil was dissolved in ethanol and the hydrochloride was precipitated with ethanolic HCl. The reaction product was purified by recrystallization from ethanol. Yield: 14.2 grams; melting point 219°–221° C.

In the same manner, starting from the appropriate starting materials, the same compounds as listed above under Example 1 are prepared.

In addition, by substituting the appropriate gamma-chlorochloro, bromo, or trifluoromethyl-butyrophenone for the F-butyrophenone starting material of Examples 1 or 2, the following additional compounds of Type I and their acid addition salts, e.g., their hydrochlorides, hydrobromides, citrates, or tartrates are prepared:

- 1-[3-(p-chlorobenzoyl)propyl]-4-(p-methylbenzoyl)-4-hydroxypiperidine.
- 1-[3-(p-chlorobenzoyl)propyl]-4-(p-methoxybenzoyl)-4-hydroxypiperidine.
- 1-[3-(p-chlorobenzoyl)propyl]-4-(p-bromobenzoyl)-4-hydroxy piperidine.
- 1-[3-(p-chlorobenzoyl)propyl]-4-(m-trifluoromethylbenzoyl)-4-hydroxypiperidine.
- 1-[3-(p-chlorobenzoyl)propyl]-4-(3-trifluoromethyl-4-chlorobenzoyl)-4-hydroxypiperidine.
- 1-[3-(p-chlorobenzoyl)propyl]-4-benzoyl-4-hydroxypiperidine.
- 1-[3-(p-chlorobenzoyl)propyl]-4-(p-chlorobenzoyl)-4-hydroxypiperidine.
- 1-[3-(p-chlorobenzoyl)propyl]-4-(3,4-dichlorobenzoyl)-4-hydroxypiperidine.
- 1-[3-(p-chlorobenzoyl)propyl]-4-(3,4-dimethylbenzoyl)-4-hydroxypiperidine.
- 1-[3-(p-chlorobenzoyl)propyl]-4-(p-fluorobenzoyl)-4-hydroxypiperidine.
- 1-[3-(m-chlorobenzoyl)propyl]-4-(p-methylbenzoyl)-4-hydroxypiperidine.
- 1-[3-(o-chlorobenzoyl)propyl]-4-(p-bromobenzoyl)-4-hydroxypiperidine.
- 1-[3-(o,p-dichlorobenzoyl)propyl]-4-(m-trifluoromethylbenzoyl)-4-hydroxypiperidine.
- 1-[3-(o-bromobenzoyl)propyl]-4-(3-trifluoromethyl-4-chlorobenzoyl)-4-hydroxypiperidine.
- 1-[3-(o-fluorobenzoyl)propyl]-4-benzoyl-4-hydroxypiperidine.
- 1-[3-(m-fluorobenzoyl)propyl]-4-(p-chlorobenzoyl)-4-hydroxypiperidine.
- 1-[3-(o,p-difluorobenzoyl)propyl]-4-(3,4-dichlorobenzoyl)-4-hydroxypiperidine.
- 1-[3-(p-trifluoromethyl/benzoyl propyl]-4-hydroxypiperidine.
- 1-[3-(p-bromobenzoyl)propyl]-4-(p-methylbenzyl)-4-hydroxypiperidine.
- 1-[3-(p-bromobenzoyl)propyl]-4-(p-methoxybenzoyl)-4-hydroxypiperidine.
- 1-[3-(p-bromobenzoyl)propyl]-4-(p-bromobenzoyl)-4-hydroxypiperidine.
- 1-[3-(p-bromobenzoyl)propyl]-4-(m-trifluoromethylbenzoyl)-4-hydroxypiperidine.
- 1-[3-(p-bromobenzoyl)propyl]-4-(3-trifluoromethyl-4-chlorobenzoyl)-4-hydroxypiperidine.
- 1-[3-(p-bromobenzoyl)propyl[-4-benzoyl-4-hydroxypiperidine.
- 1-[3-(p-bromobenzoyl)propyl]-4-(p-chlorobenzoyl)-4-hydroxypiperidine.
- 1-[3-(p-bromobenzoyl)propyl]-4-(3,4-dichlorobenzoyl)-4-hydroxypiperidine.
- 1-[3-(p-bromobenzoyl)propyl]-4-(3,4-dimethylbenzoyl)-4-hydroxypiperidine.
- 1-[3-(m-trifluoromethylbenzoyl)propyl]-4-(p-methylbenzoyl)-4-hydroxypiperidine.
- 1-[3-(m-trifluoromethylbenzoyl)propyl]-4-(p-methoxybenzoyl)-4-hydroxypiperidine.

1-[3-(m-trifluoromethylbenzoyl)propyl-4-(p-bromobenzoyl)-4-hydroxypiperidine.
1-[3-(m-trifluoromethylbenzoyl)propyl]-4-(m-trifluoromethylbenzoyl)-4-hydroxypiperidine.
1-[3-(m-trifluoromethylbenzoyl)propyl]-4-(3-trifluoromethyl-4-chlorobenzoyl)-4-hydroxypiperidine.
1-[3-(m-trifluoromethylbenzoyl)propyl]-4-benzoyl-4-hydroxypiperidine.
1-[3-(m-trifluoromethylbenzoyl)propyl]-4-(p-chlorobenzoyl)-4-hydroxypiperidine.
1-[3-(m-trifluoromethylbenzoyl)propyl]-4-(3,4-dichlorobenzenzoyl)-4-hydroxypiperidine.
1-[3-(m-trifluoromethylbenzoyl)propyl]-4-(3,4-dimethylbenzoyl)-4-hydroxypiperidine.
1-[3-(p-fluorobenzoyl)propyl]-4-(3,5-ditrifluoromethylbenzoyl)-4-hydroxypiperidine.

EXAMPLE 3:
4-BUTYRYLOXY-4-(p-FLUOROBENZOYL)-1-[3-(p-FLUOROBENZOYL)PROPYL]PIPERIDINE HYDROCHLORIDE

A mixture of 3.87 grams (0.01 mole) of 1-[3-(p-fluorobenzoyl)propyl]-4-(p-fluorobenzoyl)-4-hydroxy piperidine; 15.8 grams (0.10 mole) of butyric anhydride, 1.5 grams (0.015 mole) of triethylamine and 0.3 grams (0.002 mole) of 4-pyrrolidinopyridine was heated for six hours at 40° C. Excess anhydride and triethylamine was removed under reduced pressure. The residue was dissolved in ethylacetate and treated with ethanolic HCl. The solid which precipitated was collected by filtration and recrystallized from ethanol to give 3.8 grams of 4-butyryloxy-4-(p-fluorobenzoyl)-1-[3-(p-fluorobenzoyl)propyl]piperidine hydrochloride. Melting point 204°–206° C.

EXAMPLE 4:
1-[3-(p-FLUOROBENZOYL)PROPYL]-4-(p-METHYLBENZOYL)-4-DIMETHYLACETOXYPIPERIDINE HYDROCHLORIDE

In the same manner as given in Example 3, this product is produced from the second product given in Example 1 and dimethylacetic anhydride In the same manner as given in Examples 3 and 4, additional 4-acyloxy compounds of any Type I compound, as set forth in Table III, are produced from the appropriate 4-hydroxy compound of Formula I and the selected anhydride, including the acetates, propionates, butyrates, caproates, valerates, heptanoates, octanoates, decanoates, dodecanoates, hexadecanoates, octodecanoates, nonadecanoates, and the like. See Table III for other representative examples.

Moreover, in addition to the substituents R and $R_1$ shown in Table III, the same and/or additional substituents as $R_1$ may be present as $R_2$ in different and varying ring positions, e.g., in a different position or as the second substituent in the benzene ring in addition to the $R_1$ substitutent already present therein, or as the R substituent in the other benzene ring, such as fluoro, bromo, chloro, and trifluoromethyl, for either R or $R_2$, and methyl, ethyl, chloro, amyl, methoxy, ethoxy, amyloxy, or the like, for $R_2$, depending only upon a predetermined selection of the ring positions and substituents present in a starting substituted or disubstituted benzene compound to be employed in Preparations 1–7 and 8–12, as will be apparent and fully within the ability of one skilled in the art, including the acid addition salts, e.g., the hydrochlorides, hydrobromides, citrates, or tartartes of such compounds.

EXAMPLES 5 – 16:

In the same manner, as shown in the following Table III, the following end products are produced, starting only with the suitable selected starting compounds of Formulas II and III or II and IV, the 4-(substituted benzoyl)-4-hydroxypiperidine (II) and the alpha-substituted-gamma-(substituted benzoyl)propane (III) or an alkylene ketal thereof (IV), as illustrated by Examples 1 and 2, or by esterification of a selected 4-hydroxy compound, as below indicated.

EXAMPLE 5:
1-[3-(p-FLUOROBENZOYL)PROPYL]-4-BENZOYL-4-HYDROXYPIPERIDINE HYDROCHLORIDE.

EXAMPLE 6:
1-[3-(p-FLUOROBENZOYL)PROPYL]-4-(p-METHYLBENZOYLOXY-4-HYDROXYPIPERIDINE HYDROCHLORIDE.

EXAMPLE 7:
1-[3-(p-FLUOROBENZOYL)PROPYL]-4-(3,4-DIMETHYLBENZOYLOXY)-4-HYDROXYPIPERIDINE HYDROCHLORIDE.

EXAMPLE 8:
1-[3-(p-FLUOROBENZOYL)PROPYL]-4-(p-METHOXYBENZOYL)-4-HYDROXYPIPERIDINE HYDROCHLORIDE.

EXAMPLE 9:
4-PROPIONYLOXY-4-(p-METHOXYBENZOYL)-1-[3-(p-FLUOROBENZOYL)PROPYL]PIPERIDINE HYDROCHLORIDE.

This compound is obtained following the procedure of Example 3 and using the corresponding p-methoxybenzoyl compound as starting material.

EXAMPLE 10:
4-PROPIONYLOXY-4-(p-FLUOROBENZOYL)-1-[3-(p-FLUOROBENZOYL)PROPYL]PIPERIDINE HYDROCHLORIDE.

This compound is obtained following the procedure of Example 3 by substituting propionic acid anhydride for butyric anhydride.

EXAMPLE 11:
4-OCTANOYLOXY-4-(p-FLUOROBENZOYL)-1-[3-(p-FLUOROBENZOYL)PROPYL]PIPERIDINE HYDROCHLORIDE.

This compound is obtained following the procedure of Example 3 by substituting octanoic acid anhydride for butyric anhydride.

EXAMPLE 12:
1-[3-(p-FLUOROBENZOYL)PROPYL]-4-(p-CHLOROBENZOYL)-4-HYDROXYPIPERIDINE HYDROCHLORIDE.

EXAMPLE 13:
1-[3-(p-FLUOROBENZOYL)PROPYL]-4-(3,4-DICHLOROBENZOYL)-4-HYDROXYPIPERIDINE HYDROCHLORIDE.

EXAMPLE 14:
1-[3-(p-FLUOROBENZOYL)PROPYL]-4-(p-BROMOBENZOYL)-4-HYDROXYPIPERIDINE HYDROCHLORIDE.

EXAMPLE 15:
1-[3-(p-FLUOROBENZOYL)PROPYL]-4-(m-TRIFLUOROMETHYLBENZOYL)-4-HYDROXYPIPERIDINE HYDROCHLORIDE.

EXAMPLE 16:
1-[3-(p-FLUOROBENZOYL)PROPYL]-4-(3-TRIFLUOROMETHYL-4-CHLOROBENZOYL9-4-HYDROXYPIPERIDINE HYDROCHLORIDE.

PHARMACOLOGY

Representative compounds of the present invention have been subjected to a series of pharmacological tests, which are suitable for measuring, inter alia:

a. Inhibition of climbing in mice (inhibition of exploratory behavior).

b. Inhibition of conditioned behavior in rats.

These tests have been described, and the importance of coordinating the compounds with these tests and the activities shown thereby is described in detail in the following literature:

a. Inhibition of Exploratory Behavior (Climbing) van Rossum, J.M., et al., in The Neuroleptics, Modern Problems of Pharmaco-Psychiatri, Vol. 5, p. 26 (1970).

Kneip, P., in Arch. Int. Pharmacodyn 126, 238 (1960).

Sandberg, S., in Arzneimittelforschung 9, 203 (1958).

b. Inhibition of Conditioned Avoidance Response "Neuroleptics characteristically interrupt the response to the warning stimulus (avoidance) without at the same time interrupting the response to the noxious stimulus (escape) which follows it." An introduction to Psycho-Pharmacology, Eds. Rech and Moore, New York, p. 264 (1971); Courvoisier, S., et al., in Arch. Int. Pharmacodyn. 92, 305 (1953); Jacobsen, E., in Psychlotrophic Drugs, Eds. Garattini, Ghetti, Amsterdam, p. 119 (1957). Jacobsen and Sonne, in Acta Pharmacol. et Toxicol. 11, pp. 135–147 (1955).

The results are tabulated in Table I, which illustrates the pharmacological activities of the compounds of the present invention.

TABLE I

R—⟨phenyl⟩—CO—(CH$_2$)$_3$—N⟨piperidine with OH⟩—CO—⟨phenyl⟩—R$_1$  × HCl

R = para-fluoro

| Compound 4-R$_1$ | Acute Toxicity in Mice LD$_{50}$ (mg/kg), 48 hours s.c. | | Inhibition of Conditioned Avoidance Response a) in rats ED$_{50}$ (mg/kg), 1.5 hrs. s.c. | Inhibition of Exploratory Behavior b) in mice ED$_{50}$ (mg/kg) 1 hr. s.c. |
|---|---|---|---|---|
| | s.c. | p.o. | | |
| CH$_3$ | >1000 | >1000 | 0.32 | 0.80 |
| OCH$_3$ | >1000 | 890 | 0.24 | 1.0 |
| F | >1000 | 500 | 0.13 | 0.19 |
| Cl | >1000 | 630 | 0.37 | 0.95 |

Although the R = para-fluoro compounds generally, and the given compounds particularly, are preferred, it is to be understood that the compounds of Table I are not listed for purposes of limiting the invention thereto, but only to exemplify dramatically the useful properties of all of the compounds within the scope of Formula I, including the 4-esters and therapeutically active acid addition salts of the compounds of Formula I.

The advantages of the compounds of the invention are as follows:

1. The new compounds possess potent CNS (central nervous system) depressant and neuroleptic properties with pronounced antipsychotic, antimanic, tranquillizing, and anxiolytic effects when administered as such or in the form of acid addition salts, such as the hydrochloride.

2. The toxicity of these compounds is very low.

3. The compounds are extremely potent antagonists of amphetamine. The cataleptogenic effect is extremely low when compared with the amphetamine-antagonistic effect. Further, these compounds block conditioned avoidance responses and inhibit exploratory activity in animals. They also inhibit aggression in isolated male mice.

Additional references are as follows:

Amphetamine Antagonism

Randrup, A., et al., in Acta Pharmacol. (KPH), 20, 145 (1963).

Randrup, A., in the Neuroleptics, Modern Problems of Pharmaco-Psychiatri, Vol. 5, p. 60 (1970).

The Cataleptogenic Effect

Rossum, J.M., et al., in The Neuroleptics, Modern Problems of Pharmaco-Psychiatri, Vol. 5, p. 26, (1970).

Stille, C., in Schweig, Med. Wochenschrift 99, 1645 (1969).

Inhibition of Aggression

Valzelli, L., in Aggressive Behaviour, Eds. Garattini and Sigg, p. 70 (1969).

Valzelli, L., in Neuro-Psycho-Pharmacology, Ed. Brill, p. 781 (1967).

4) The compounds have only weak effects on the autonomic nervous system and the cardiovascular system. Some of the compounds also possess analgetic and antiarrythmic activities.

The new compounds or their acid addition salts such as the hydrochloride can be administered per os, e.g., in the form of pills or tablets, as further detailed hereinafter. Pharmacological and clinical results indicate that the compounds of the invention will be of special value in the treatment of various mental disturbances, e.g., psychosis, mania, or neurosis.

For many purposes, a suitable clinical dose is between 0.1 – 25 mg. Naturally, the dosage must be adjusted in accord with the condition, age, and weight of the patient.

Their general tranquilizing properties also make the new compounds suitable for veterinary applications; for instance, they are also useful for calming animals.

The high order of activity of the active agents of the present invention has been evidenced by tests in lower animals and representative of these are reported herein.

The novel compounds are preferably used in the form of their pharmaceutically-acceptable acid addition salts, e.g., their hydrochlorides, hydrobromides, or the like. The salt form is also the best form for pharmaceutical formulations. Innumerable other pharmaceutically-acceptable acid addition salts can be prepared from the hydrochlorides via the free bases inconventional manner. For oral use, the compounds are usually administered as tablets in which they are present together with usual pharmaceutical carriers, excipients, binders, and the like. For example, tablets may be prepared conventionally by compounding one of the new compounds, preferably in the form of an acid addition salt thereof, with customary carriers and adjuvants, e.g., talc, magnesium stearate, starch, lactose, gelatin, gums, and the like.

In their most advantageous form, then, the compositions of the present invention will contain a non-toxic pharmaceutical carrier in addition to the active ingredient of Formula I. Exemplary carriers are:

Solids: lactose, magnesium stearate, calcium stearate, starch, terra alba, dicalcium phosphate, sucrose, talc, stearic acid, gelatin, agar, pectin, acacia, or the like;

Liquids: peanut oil, sesame oil, olive oil, water, or the like. The active agents of the invention can be most conveniently administered in such compositions containing about 0.01 to 67 percent, preferably 0.04 to 12.15 percent, by weight of the active ingredient. Such formulations are representatively illustrated in U.S. Pat. No. 3,402,244.

A wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion; for parenteral administration, the composition may be a sterile solution; and for rectal administration, a suppository.

The method of using the compounds of the present invention comprises internally administering a compound of Formula I, usually in the form of a non-toxic, pharmacologically-acceptable acid addition salt, and preferably admixed with a pharmaceutical carrier, for example, in the form of any of the above-mentioned compositions, or filled into a capsule, to alleviate psychotic conditions and symptoms thereof in a living animal body, for example, the aforementioned psychotic, manic, or neurotic states. The compounds and their non-toxic salts, especially the hydrochlorides, may be advantageously employed in amounts approximating those employed for any of the three clinically-useful compounds mentioned herein. Illustratively, they may be used in an amount of about 0.1 to 200 milligrams per unit dose, preferably about 2.5 to 50 milligrams for an oral dose, usually 0.1 to 25 milligrams, while parenteral dosages are usually less and ordinarily about one-half the oral dose so that the preferred parenteral unit dosage will be about one to 25 milligrams. The unit dose is preferably given a suitable number of times daily so that the daily dose may vary from 0.3 to 600 milligrams. Preferred daily dosages will vary from about 7.5 to 150 milligrams (oral) to about three to 75 milligrams (parenteral). However, the compounds are subject to wide variations in optimum daily and unit dosages, due to patient body weight, condition, and ancillary factors, and the invention therefore should not be limited by the exact ranges stated. The exact dosage, both unit and daily, will of course have to be determined according to established medical principles. In addition, the active ingredients of the present invention or compositions containing the same may either be administered together with or include other physiologically active materials and/or medicaments, e.g., buffering agents, antacids, sedatives, stimulants, anticholinergics, analgesics, or the like.

The following formulations are representative for all of the pharmacologically active compounds of the invention, but have been particularly designed to embody as active ingredient the particular compound embodied therein, and especially a pharmacologically acceptable salt thereof, for example, its tartrate, hydrochloride, hydrobromide, fumarate, or like pharmacologically acceptable salt.

As already stated, for oral use the compounds are usually administered as tablets, although other forms may be employed. Tablets may be made by compounding one of the compounds of the invention, preferably as an acid-addition salt, with customary carriers and adjuvants, e.g., talc, magnesium stearate, starch, lactose, gelatin, gums, or the like.

The following is a suitable tablet formulation:
  0.1 – 1 gram of 1-[3-(p-fluorobenzoyl)-propyl]-4-(p-fluorobenzoyl)-4-hydroxypiperidine hydrochloride
  9 grams of potato starch
  1 gram of colloidal silica
  2 grams of talc
  0.2 gram of magnesium stearate
  2.5 gram of 5% aqeuous solution of gelatin.

This mixture is made up into 100 tablets, each containing 1 – 10 mg of the active component.

The pharmacologically active compounds provided by the present invention may also be administered successfully by embodying an effective quantity thereof in an injectable emulsion or suspension for injection into an animal body, in oral powders, suspension or syrups, and in other acceptable dosage forms, such as solutions in propylene glycol.

Although very small quantities of the active materials of the present invention are effective when minor therapy is involved or in cases of administration to subjects having a relatively low body weight, unit dosages are usually five milligrams or above, and preferably twenty-five, fifty, or one hundred milligrams, or even higher, depending of course upon the emergency of the situation and the particular result desired. To repeat, the exact individual dosages as well as daily dosages in a particular case will of course be determined according to established medical principles and under the supervision of the physician or veterinarian involved.

Representative compounds of the invention, including important intermediates for their production, are set forth in Tables II and III.

TABLE II x HCl

| 4-$R_1$ | 3-$R_2$ | M.p., °C.[a] | Preparation Route |
|---|---|---|---|
| H | H | 230 – 233 | Ba — Ca |
| $CH_3$ | H | 232 – 235 | Ba — Ca |
| $CH_3$ | $CH_3$ | 190 – 192 | Ba — Ca |
| $OCH_3$ | H | 218 – 220 | Ba — Ca |
| F | H | 241 – 243 | Ba — Ca |
| Cl | H | 205 – 208 | Ba — Ca |
| Cl | Cl | 210 – 212 | Bb — Ca |
| Br | H | 246 – 248 | Ba — Ca |
| H | $CF_3$ | 236 – 238 | Bb — Ca |
| Cl | $CF_3$ | 250 decomp. | Bb — Ca |

[a]Melting points are uncorrected

TABLE III

R = para-fluoro x HCl I

| 4-$R_1$ | 3-$R_2$ | $R_4$ | M.p., °C.[a] |
|---|---|---|---|
| H | H | H | 215–217 |
| $CH_3$ | H | H | 228–230 |
| $CH_3$ | $CH_3$ | H | 219–221 |
| $OCH_3$ | H | H | 190–192 |
| $OCH_3$ | H | $C_2H_5CO$ | 221–223 |
| F | H | H | 219–221 |
| F | H | $C_2H_5CO$ | 206–208 |
| F | H | $C_3H_7CO$ | 204–206 |
| F | H | $C_7H_{15}CO$ | 191–193 |
| Cl | H | H | 208–210 |
| Cl | Cl | H | 195–197 |
| Br | H | H | 215–217 |
| H | $CF_3$ | H | 180–182 |
| Cl | $CF_3$ | H | 207–209 |

[a]Melting points are uncorrected

Various modifications in the compounds, compositions, and methods of the invention will be apparent to one skilled in the art and may be made without departing from the spirit or scope thereof, and it is therefore to be understood that the invention is to be limited only by the scope of the appended claims.

We claim:
1. A compound selected from the group consisting of a. 1-(3-benzoylpropyl)-4-benzoyl-4-hydroxy or -4-acyloxypiperidines having the formula

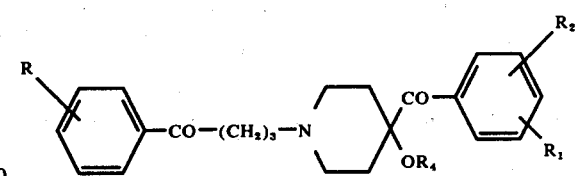

I wherein
$R_1$ and $R_2$ independently represent hydrogen, a loweralkyl group of one to five carbon atoms inclusive, fluorine, chlorine, bromine, loweralkoxy of one to five carbon atoms inclusive, or trifluoromethyl,
$R_4$ represents hydrogen or an acyl group of two to nineteen carbon atoms inclusive, and
R represents fluorine, chlorine, bromine, or trifluoromethyl, and
b. acid addition salts thereof.
2. Pharmacologically acceptable acid addition salt of a basic piperidine ketone of claim 1.
3. Compound of claim 1 wherein $R_1$ is methyl and $R_2$ is hydrogen.
4. Compound of claim 1 wherein $R_1$ is methoxy and $R_2$ is hydrogen.
5. Compound of claim 1 wherein $R_1$ is fluoro and $R_2$ is hydrogen.
6. Compound of claim 1 wherein $R_1$ is bromo and $R_2$ is hydrogen.
7. Compound of claim 1 wherein $R_1$ is trifluoromethyl and $R_2$ is hydrogen.
8. Compound of claim 1 wherein $R_1$ is hydrogen and $R_2$ is hydrogen.
9. Compound of claim 1 wherein $R_1$ is chloro and $R_2$ is hydrogen.
10. Compound of claim 1 wherein $R_1$ is chloro and $R_2$ is trifluoromethyl.
11. Compound of claim 1 wherein $R_1$ is methyl and $R_2$ is methyl.
12. Compound of claim 1 wherein $R_1$ is chloro and $R_2$ is chloro.
13. Compound of claim 1 wherein R is fluoro.
14. Compound of claim 1 wherein $R_4$ is hydrogen.
15. Compound of claim 1 which is 1-[3-(p-fluorobenzoyl)propyl]-4-(p-fluorobenzoyl)-4-hydroxypiperidine acid addition salt.
16. Compound of claim 1 which is 1-[3-(p-fluorobenzoyl)-propyl]-4-(p-fluorobenzoyl)-4-hydroxypiperidine hydrochloride.
17. Compound of claim 1 which is 4-loweralkanoyloxy-4-(p-fluorobenzoyl)-1-[3-(p-fluorobenzoyl)-propyl]-piperidine acid addition salt.
18. Compound of claim 1 which is 4-propionyloxy-4-(p-fluorobenzoyl)-1-[3-(p-fluorobenzoyl)-propyl]-piperidine acid addition salt.
19. Compound of claim 1 which is 1-[3-(p-fluorobenzoyl)-propyl]-4-(p-methylbenzoyl)-4-hydroxypiperidine acid addition salt.
20. Compound of claim 1 which is 1-[3-(p-fluorobenzoyl)-propyl]-4-(p-methoxybenzoyl)-4-hydroxypiperidine acid addition salt.

21. Compound of claim 1 which is 1-[3-(p-fluorobenzoyl)-propyl]-4-(p-bromobenzoyl)-4-hydroxypiperidine acid addition salt.

22. Compound of claim 1 which is 1-[3-(p-fluorobenzoyl)propyl]-4-(m-trifluoromethylbenzoyl)-4-hydroxypiperidine acid addition salt.

23. Compound of claim 1 which is 1-[3-(p-fluorobenzoyl)-propyl]-4(3-trifluoromethyl-4-chlorobenzoyl)-4-hydroxypiperidine hydrochloride.

24. Compound of claim 1 which is 1-[3-(p-fluorobenzoyl)-propyl]-4-benzoyl-4-hydroxypiperidine acid addition salt.

25. Compound of claim 1 which is 1-[3-(p-fluorobenzoyl)-propyl]-4-(p-chlorobenzoyl)-4-hydroxypiperidine acid addition salt.

26. Compound of claim 1 which is 4-butyryloxy-4-(p-fluorobenzoyl)-1-[3-(p-fluorobenzoyl)-propyl]-piperidine acid addition salt.

27. Compound of claim 1 which is 4-octanoyloxy-4-(p-fluorobenzoyl)-1-[3-(p-fluorobenzoyl)-propyl]-piperidine acid addition salt.

28. Compound of claim 1 which is 4-propionyloxy-4-(p-methoxybenzoyl)-1-[3-(p-fluorobenzoyl)-propyl]-piperidine hydrochloride.

29. Compound of claim 1 which is 1-[3-(p-fluorobenzoyl)-propyl-4-(3,4-dichlorobenzoyl)-4-hyroxypiperidine acid addition salt.

30. Compound of claim 1 which is 1-[3-(p-fluorobenzoyl)-propyl]-4-(3,4-dimethylbenzoyl)-4-hydroxypiperidine acid addition salt.

31. A pharmaceutical composition suitable for use in the alleviation of psychotic conditions comprising a compound of claim 1, in an amount effective for said purpose, in association with a pharmaceutical carrier.

32. Method for the treatment of a patient suffering from a psychotic, manic, or neurotic state, comprising administering to the patient a compound of claim 1 in an amount effective for the alleviation of said condition.

* * * * *

UNITED STATES PATENT OFFICE
CERTIFICATE OF CORRECTION

Patent No. 4,021,564      Dated May 3, 1977

Inventor(s) Sven Erik Harry Hernestam, Anders Karl Konrad Björk, Aina Lisbeth Abramo and Bengt Erik Sigvard Kjellberg It is certified that error appears in the above-identified patent and that said Letters Patent are hereby corrected as shown below:

Column 7, line 62; after the word "piperidine" and before the word "precipitated", insert ---hydrobromide---.

Signed and Sealed this

*Eleventh* Day of *October 1977*

[SEAL]

*Attest:*

RUTH C. MASON
*Attesting Officer*

LUTRELLE F. PARKER
*Acting Commissioner of Patents and Trademarks*

UNITED STATES PATENT OFFICE
CERTIFICATE OF CORRECTION

Patent No. 4,021,564  Dated May 3, 1977

Inventor(s) Sven Erik Harry Hernestam, Anders Karl Konrad Björk, Aina Lisbeth Abramo and Bengt Erik Sigvard Kjellberg It is certified that error appears in the above-identified patent and that said Letters Patent are hereby corrected as shown below:

Column 2, line 28; change "loweralkyl" to read ---lower-alkyl---.

Column 11, line 14; change "225 of ethanol" to read ---225 ml of ethanol---.

Column 12, lines 45-46; change "1-[3-(p-trifluoromethyl benzoyl)propyl]-4- hydroxypiperidine." to read ---1-[3-(p-trifluoromethyl benzoyl)propyl]-4-(3,4-dimethylbenzoyl)-4-hydroxypiperidine.---

Column 12, line 47; change "(p-methylbenzyl)-" to read ---(p-methylbenzoyl)- ---.

Column 13, line 13; change "dichlorobenzenzoyl)-" to read ---dichlorobenzoyl)- ---.

Column 14, line 2; change "tartartes" to read ---tartrates---.

Column 15, line 38; change "CHLOROBENZOYL9-4-" to read ---CHLOROBENZOYL)-4- ---.

Column 15, line 68; change "Psychlotrophic Drugs," to read ---Psychotrophic Drugs,---.

Signed and Sealed this

Eighteenth Day of April 1978

[SEAL]

Attest:

RUTH C. MASON
Attesting Officer

LUTRELLE F. PARKER
Acting Commissioner of Patents and Trademarks